United States Patent [19]

Paul

[11] Patent Number: 5,314,432
[45] Date of Patent: May 24, 1994

[54] LUMBAR SPINAL DISC TROCAR PLACEMENT DEVICE

[76] Inventor: Kamaljit S. Paul, 3220 Old Orchard La., Oshkosh, Wis. 54901

[21] Appl. No.: 102,201

[22] Filed: Aug. 5, 1993

[51] Int. Cl.⁵ .............................................. A61B 17/00
[52] U.S. Cl. .................................... 606/130; 606/1; 128/DIG. 26
[58] Field of Search .......... 606/130, 1, 96–98, 606/102, 104; 128/653.1–653.5, DIG. 26; 604/116

[56] References Cited

U.S. PATENT DOCUMENTS

| | | |
|---|---|---|
| 3,964,480 | 6/1976 | Froning . |
| 4,638,799 | 1/1987 | Moore . |
| 4,733,661 | 3/1988 | Palestrant ............................ 604/116 |
| 4,750,487 | 6/1988 | Zanetti . |
| 4,841,967 | 6/1989 | Chang et al. ........................ 606/130 |
| 4,846,173 | 7/1989 | Davidson ............................ 606/130 |
| 4,883,053 | 11/1989 | Simon .................................. 606/130 |
| 5,047,036 | 9/1991 | Koutrouvelis ..................... 606/130 |
| 5,080,662 | 1/1992 | Paul ..................................... 606/130 |
| 5,100,411 | 3/1992 | Koutrouvelis ..................... 604/116 |
| 5,196,019 | 3/1993 | Davis et al. ......................... 606/130 |
| 5,242,455 | 9/1993 | Skeens et al. ...................... 606/130 |

Primary Examiner—Stephen C. Pellegrino
Assistant Examiner—Glenn Dawson
Attorney, Agent, or Firm—Depaoli & O'Brien

[57] ABSTRACT

This invention provides a stereotactic device which is adapted for placement of a medical probe in the performance of percutaneous lumbar discectomy in a human body. The stereotactic device is utilized in conjunction with a fluoroscope for alignment and placement of a trocar type probe into a herniated disc. Bubble gauges are employed to level the x-axis and y-axis of a trocar support, which orients and slidably guides the medical probe into the targeted herniated disc nucleus.

8 Claims, 5 Drawing Sheets

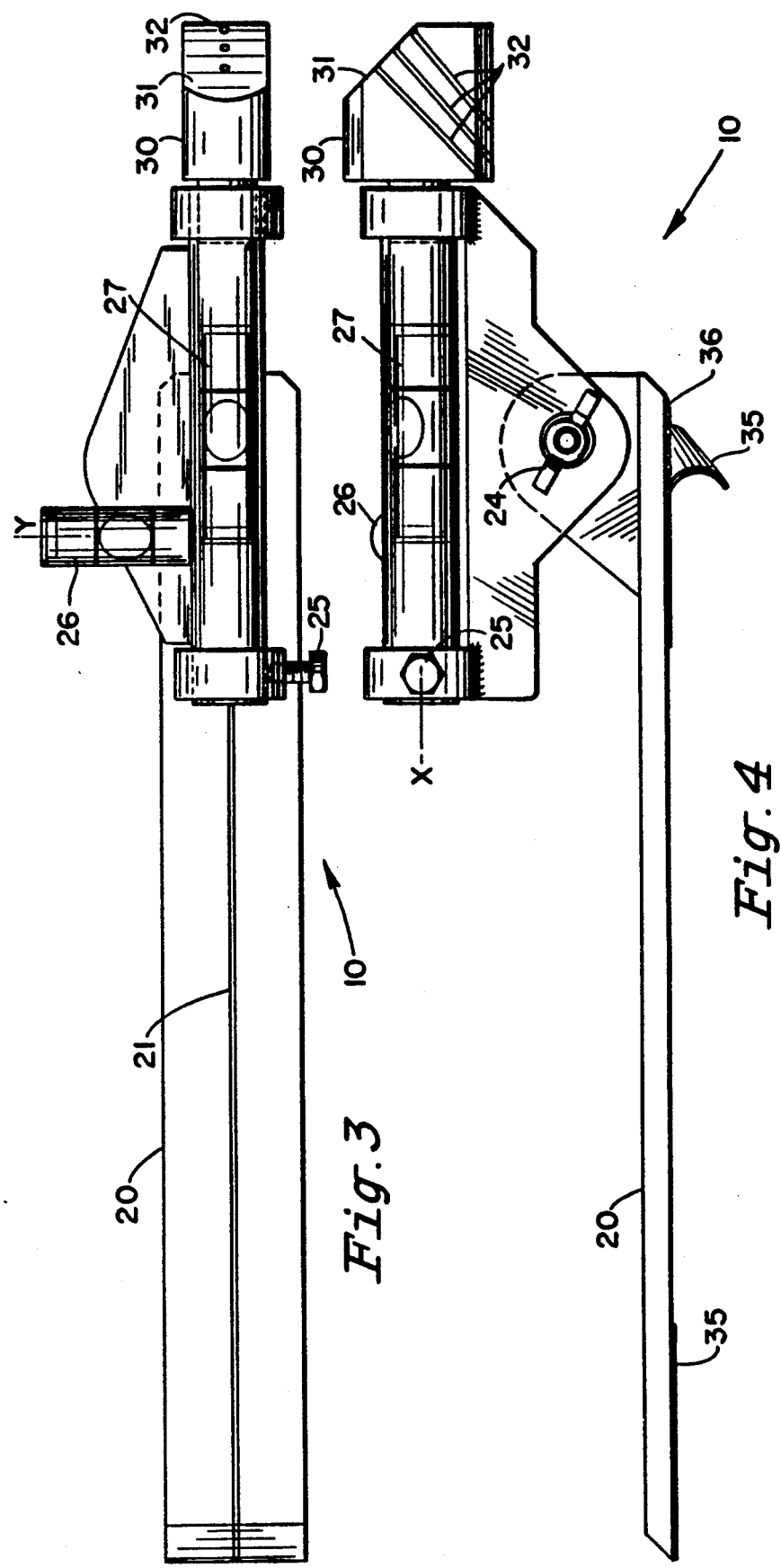

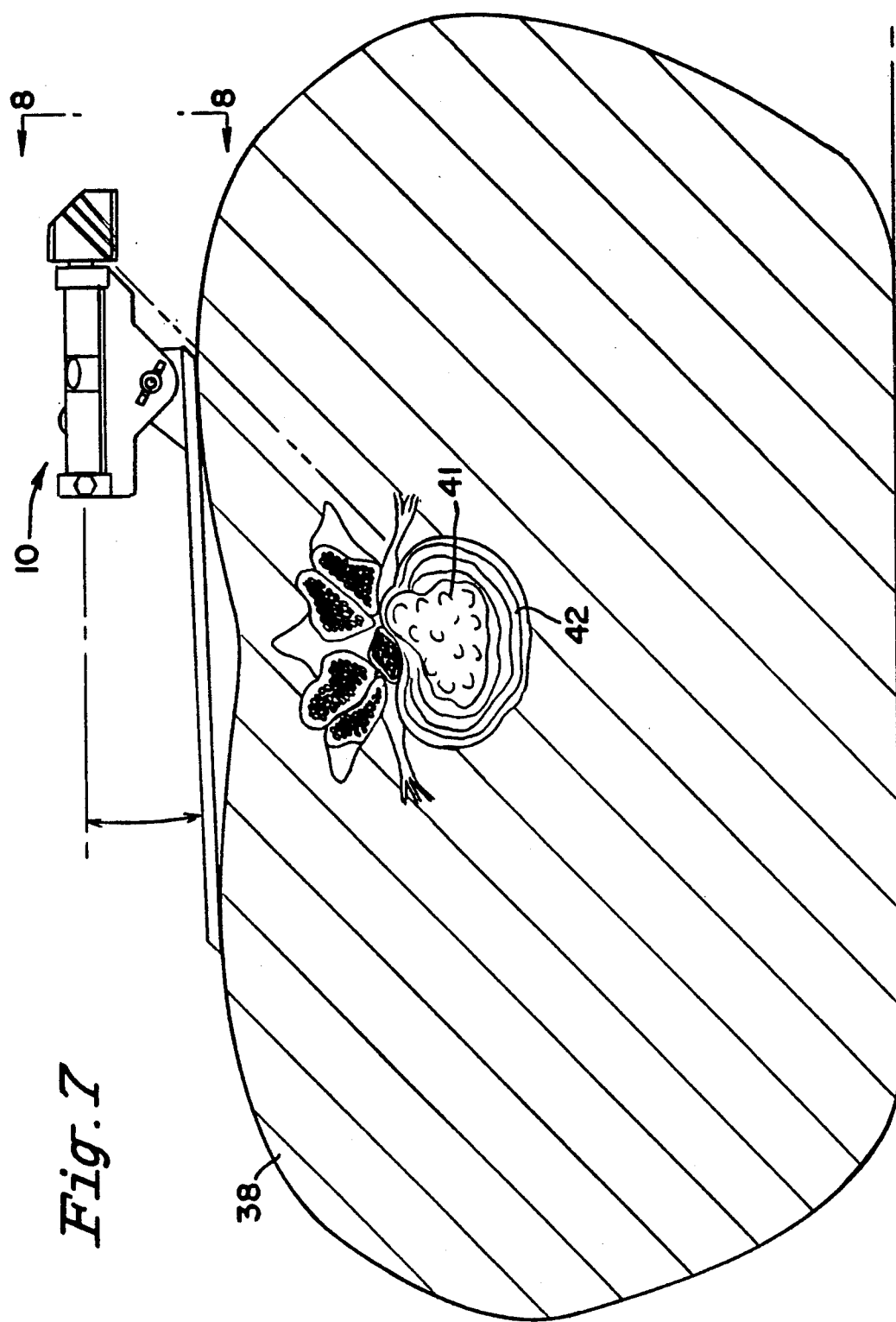

LUMBAR SPINAL DISC TROCAR PLACEMENT DEVICE

BACKGROUND OF THE INVENTION

A common problem among sufferers of back pain is a prolapsed lumbar intervertebral disc, wherein a portion of the disc between two vertebrae in the lower back prolapses outward and causes pressure on a nerve. One method of treatment is by major surgery. Because of the substantial trauma caused by such surgery, it is common for the patient to experience a recovery period of ten to twelve weeks.

Recently a new technique has been developed wherein nucleus material of the prolapsed disc is excised by percutaneous aspiration. The disc nucleus is soft and jelly-like in consistency, and can be resected and aspirated by use of a specially designed cannula. The aspiration cannula is inserted into the nucleus of the prolapsed disc with the aid of a trocar probe, prior to connection of the cannula to an aspirating machine. A major concern is precise placement of the probe to avoid nerve damage.

Since herniation of a disc most frequently occurs between the fourth and fifth lumbar vertebrae, or between the fifth lumbar and sacral vertebrae, the insertion of the probe is very difficult. Particularly in the latter case, the probe must be inserted not only at an angle to the vertical, but also at an angle relative to the sagittal axis, in order to avoid the protective iliac crest of the sacrum. Preferably the probe is inserted at about eight centimeters away from the midline, on the coronal plane of the prolapsed disc level, at an angle of about 45 degrees. In the past, the probe has been inserted by trial and error, while monitoring its placement by fluoroscopic examination.

Devices and means for stereotactic positioning and guiding of a medical probe to a herniated lumbar disc are described in U.S. Pat. Nos. 3,964,480; 4,638,799; 4,750,487; 5,047,036; and 5,080,662. The systems mainly have in common a stereotactic bridge or mounting structure which is attached to an operating or C.T. scan type table. Such structures are mechanically complex, and have limited range of mobility.

There remains a need for new and improved devices to overcome the various difficulties associated with automated percutaneous lumbar discectomy procedures.

Accordingly, it is an object of this invention to provide a self-contained medical probe guidance device which can be hand-manipulated on the contour surface of a human body.

It is another object of this invention to provide a mobile stereotactic device for fluoroscope-monitored alignment and placement of a medical probe for percutaneous lumbar discectomy in a human body.

Other objects and advantages of the present invention shall become apparent from the accompanying description and drawings.

SUMMARY OF THE INVENTION

One or more objects of the present invention are accomplished by the provision of a stereotactic device adapted for fluoroscope-monitored alignment and placement of a medical probe for percutaneous lumbar discectomy in a human body comprising:

(a) an elongated base plate with a radiopaque reference line along a plate longitudinal axis;
(b) a trocar support means pivotally secured adjacent to one end of said base plate, and a longitudinal x-axis of said support means which is in plane alignment with the longitudinal radiopaque reference line along said base plate;
(c) leveling gauges integral to the trocar support means for leveling of the longitudinal x-axis and a y-axis of said support means; and
(d) endpiece means for trocar orientation and slidable guidance integral to and adjacent to a posterior end of said trocar support means.

The x-axis and y-axis are in perpendicular intersecting directions, and taken together form an x-y plane. The x-axis is in a longitudinal direction, and the y-axis is in a lateral direction relative to the reference line in the base plate.

BRIEF DESCRIPTION OF THE DRAWINGS

FIG. 3 is a top plan view of the FIG. 1 device.

FIG. 4 is a side elevation view of the FIG. 1 device.

FIG. 7 is a cross-section through a human body with backbone detail, and with a FIG. 1 device positioned and radially oriented on the upper surface of the body.

DESCRIPTION OF INVENTION EMBODIMENTS

Figure 1:
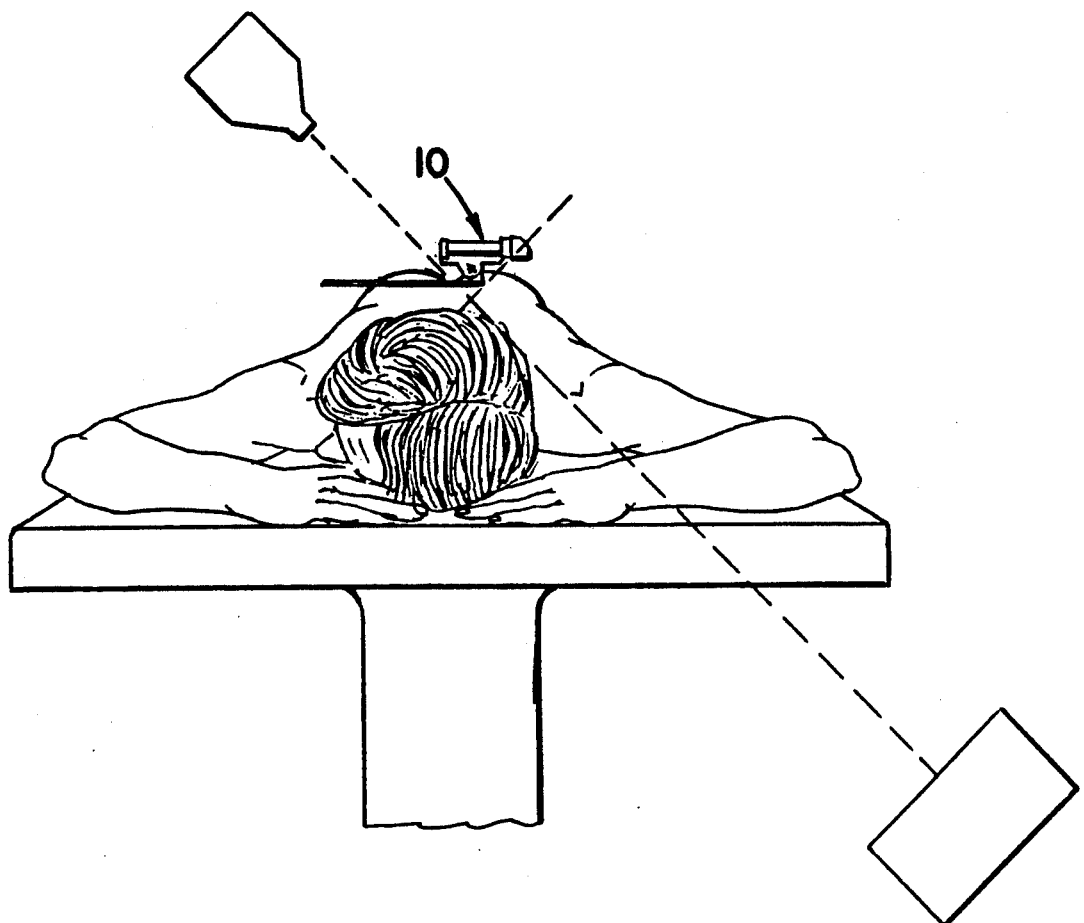
FIG. 1 is a view of a patient in a prone position on a fluoroscopic examination table with a present invention stereotactic device positioned for placement of a medical probe.

A present invention stereotactic device has dimensions which are practical for easy manipulation and placement on the skin surface of a patient, such as over the spinal area of a patient lying prone on a fluoroscopic examination table.

A typical invention device has a base plate which has dimensions of about 20–25 centimeters in length, 2–4 centimeters in width, and 0.2–0.6 centimeter in thickness.

A radiopaque reference line extends along the plate longitudinal axis. The radiopaque reference line can be a metal wire which is embedded in the surface of a radio-transparent base plate.

The base plate and other components of the stereotactic device can be fabricated with metal and/or plastic structural materials. The plastic materials can be thermoplastic polymers such as polyethylene, polypropylene, polystyrene, polycarbonate, polyurethane, polyvinyl chloride, polyamide, polyester, and the like.

The base plate can be constructed of a rigid plastic material such as poly(methyl methacrylate), or a rigidly deformable plastic such as polypropylene. A rigid base plate also can be attached to a flexible substrate such as a planar disc of polyethylene which extends laterally outward from the rigid base plate structure.

Alternatively, the base plate can have an undercoating of a contact adhesive layer for removably affixing the stereotactic device to the skin surface of a patient.

The trocar support means as illustrated in the drawings can be pivotally secured near one end of the base plate. The trocar support means is an integrated arrangement of two leveling gauges in an x-axis and y-axis conformation, in combination with an endpiece. The overall length of the trocar support means is about 10–12 centimeters. The endpiece can be a solid block of about two centimeters in cubic dimensions, with a sloped cross-sectional face as illustrated in the drawings.

The endpiece has at least one trocar-type medical probe guiding conduit, which has a straight-line annular cross-section. The guiding conduit traverses the endpiece downward at an angle of about 45° relative to the x-axis of the trocar support means, and is normal relative to the x-y plane.

In a preferred embodiment, the endpiece has at least two trocar-type medical probe guiding conduits which traverse the endpiece downward at an orientation angle in the range between about 40°–55° relative to the x-axis of the trocar support means, and the guiding conduits are in a perpendicular plane relative to the x-y plane. The diameter of a guiding conduit is slightly larger than that of the medical probe being utilized.

The trocar support assembly can have tightening means to prevent movement of the pivotal point of attachment to the base plate. The tightening means can be a turn screw or a wing-bolt unit or the like. Similarly, the trocar support means can have tightening means in combination with the leveling gauges for maintaining a leveled orientation of the x-y plane.

In FIG. 1 stereotactic device 10 is constructed of molded clear plastic components, with metal turn screw and wing-nut securing means.

Figure 2:
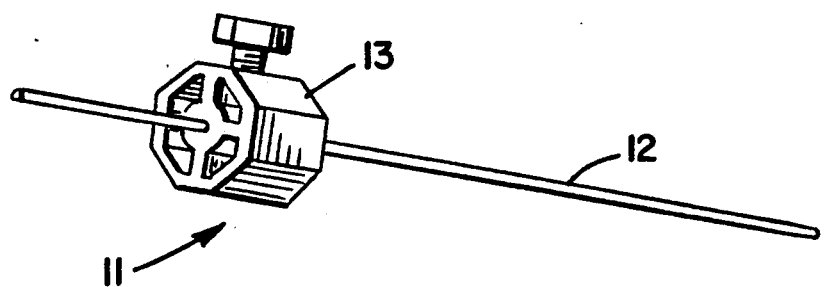
FIG. 2 is an isometric view of a trocar which is utilized as a medical probe in combination with a present invention stereotactic device.

In FIG. 2 trocar 11 consists of resilient metal probe 12 having a sharp distal end, and slidably adjustable plastic knob 13.

In FIG. 3 and FIG. 4 clear plastic base plate 20 has radiopaque reference line 21 which is an embedded metal wire. Plastic trocar support means 22 is pivotally secured to base plate 20 with metal wing-nut 24. The longitudinal x-axis of trocar support means 22 is in plane alignment with radiopaque reference line 21. Turn screw 25 is a means of securing trocar support means 22 after lateral adjustment along the y-axis with bubble gauge 26. Adjustment of the longitudinal x-axis of trocar support means 22 with bubble gauge 27 is secured with wing-screw 24.

Endpiece means 30 is a solid plastic block with a sloped cross-sectional face 31. FIG. 3 and FIG. 4 illustrate three guiding conduits 32 at varied angles between about 40°–55° relative to the x-axis of trocar support means 22.

In FIG. 4 peel strip 35 can be separated from contact adhesive 36, so that base plate 20 can be adhesively secured to skin surface when stereotactic device 10 is positioned over the spinal area of a prone patient.

Figure 8:
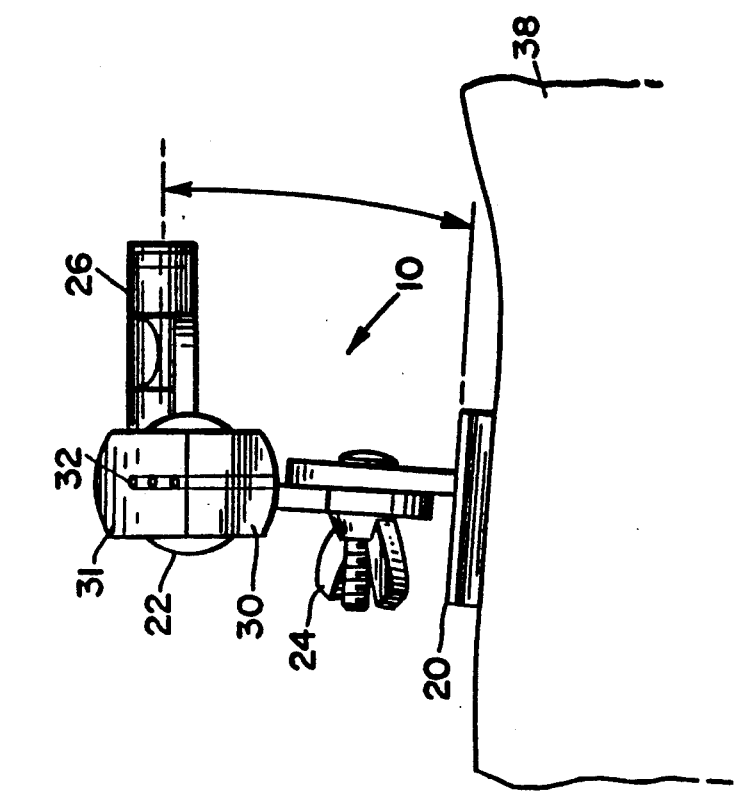
FIG. 8 is a view taken along lines 8—8 of FIG. 7 illustrating angle adjustment for device leveling on the body contours.
Figure 6:
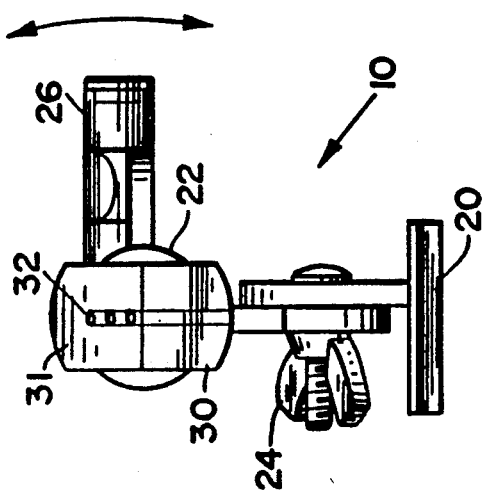
FIG. 6 is a right end elevation view of the FIG. 1 device.
Figure 5:
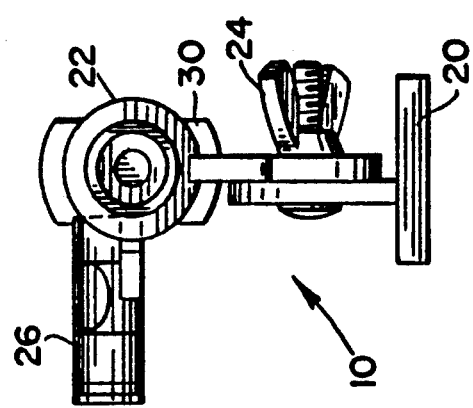
FIG. 5 is a left end elevation view of the FIG. 1 device.

FIG. 5 and FIG. 6 illustrate left end and right end elevation views of stereotactic device 10. FIG. 7 and FIG. 8 illustrate the adjusted positioning of stereotactic device 10 on human body 38 shown in a cross-sectional view. In FIG. 7 herniated nucleus pulposus 41 of disc 42 is the target site of a trocar which is oriented and guided by stereotactic device 10.

Figure 9:
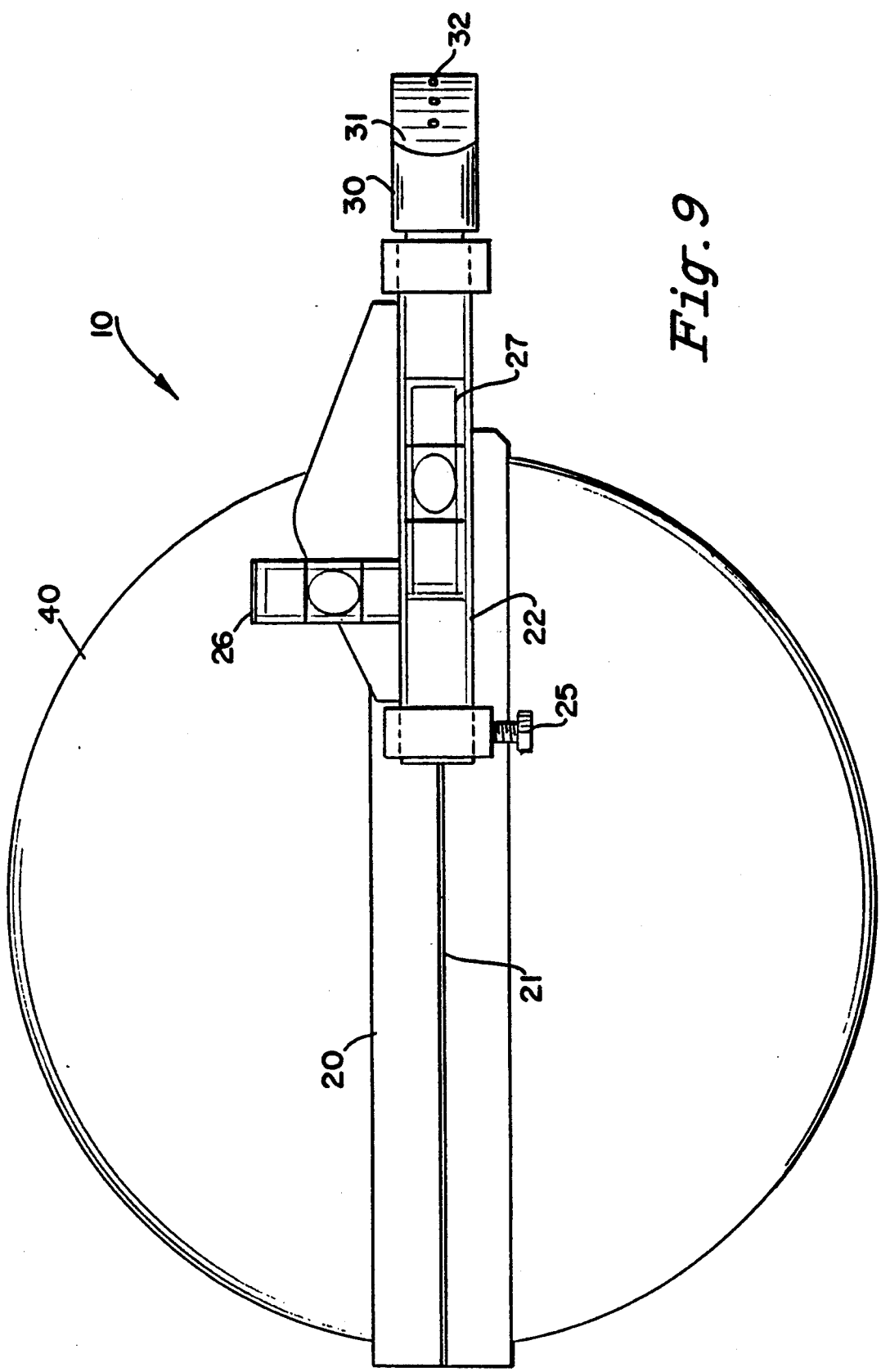
FIG. 9 is a top plan view of a present invention stereotactic device with a flexible base support which conforms to human body contours.

FIG. 9 is stereotactic device 10 having rigid base plate 20 attached to flexible support 40, which provides stable conformation to human body contours. Flexible support 40 is constructed of thin plastic or rubber matting.

A present invention stereotactic device 10 is utilized interactively with C.T. and fluoroscopic scanners to achieve accurate placement of an oriented trocar-type medical probe into a human body.

C.T. scanners are employed to provide cross-sectional internal pictures of body cavity. C.T. scanners are capable of measuring a proposed trajectory for a medical probe to within 0.1 millimeter with respect to depth, and within 0.1 degree with respect to angular orientation.

The following procedures illustrate the use of an invention stereotactic device for performing a C.T. and fluoroscope guided discectomy.

A patient is placed face-down in the prone position and preped and draped in the conventional manner. A C.T. scan is made of the suspected disc herniation.

The site of entrance in the skin surface, as well as the depth and the angle to be used, are calculated under C.T. guidance. Thin 3–5 mm axial the herniated disc. The site of entrance is marked on the skin surface.

Local anesthesia is administered in the skin, muscles, and paravertebral space. A three millimeter skin incision is made at the entrance site.

Utilizing a present invention hand-held stereotactic device for alignment and guidance, an elongated trocar is inserted slightly posteriorly into the nucleus pulposus of the herniated disc. To accomplish this percutaneous intervention, the stereotactic device is placed on the patient's back, and hand manipulated so that the trocar is guided into the body in the plane of the cross-section image developed by the C.T. scanner. After fluoroscope verification of the trocar position, the stereotactic device is disengaged from the trocar.

A straight cannula with a tapered dilator is passed over the trocar and penetrated down to the wall of the annulus. The position of the cannula and trocar is verified by fluoroscopic scan.

Incision of the annulus is made by the trephine, and then the trephine and trocar are removed from the cannula. A nucleotome ® type probe is inserted through the cannula, and suction of the annulus pulposus is performed.

A present invention stereotactic device facilitates the orientation and precise placement of a trocar-type medical probe into a herniated disc under C.T. and fluoroscope guidance. A present invention stereotactic device can be constructed of inexpensive materials, and is lightweight and amenable to hand manipulation.

What is claimed is:

1. A stereotactic device adapted for fluoroscope-monitored alignment and placement of a medical probe for percutaneous lumbar discectomy in a human body comprising:

(a) an elongated base plate with a radiopaque reference line along a plate longitudinal axis;

(b) a trocar support means pivotally secured adjacent to one end of said base plate, a longitudinal x-axis of said support means being in plane alignment with the longitudinal radiopaque reference line along said base plate;

(c) leveling gauges integral to the trocar support means for leveling of the longitudinal x-axis and a y-axis of said trocar support means, said leveling gauges being pivotable with said trocar support means relative to aid elongated base plate; and (d) endpiece means for trocar orientation and slidable guidance integral to and adjacent to a posterior end of said trocar support means.

2. A device in accordance with claim 1 wherein the base plate is flexible, and conforms to a surface contour when positioned on a human body.

3. A device in accordance with claim 1 wherein the base plate has a bottom surface with contact adhesive means.

4. A device in accordance with claim 1 wherein said base plate is a rigid structure which is attached to a surface of a flexible planar substrate means.

5. A device in accordance with claim 1 wherein the trocar support means has tightening means in combination with said leveling gauges for maintaining a leveled orientation.

6. A device in accordance with claim 1 wherein the endpiece means is selective over a trocar orientation range between about 40°–55° relative to the x-axis of said trocar support means.

7. A device in accordance with claim 1 wherein the endpiece means is a solid block with at least one trocar guiding conduit which traverses the endpiece downward at an angle of about 45° relative to the x-axis of said trocar support means, and said guiding conduit is in a plane which includes said x-axis and is perpendicular relative to the x-y plane.

8. A device in accordance with claim 1 wherein the endpiece means is a solid block with at least two trocar guiding conduits which traverse the endpiece downward at an orientation angle in the range between about 40°–55° relative to the x-axis of said trocar support means, and said guiding conduits are in a plane which includes said x-axis and is perpendicular relative to the x-y plane.

* * * * *

UNITED STATES PATENT AND TRADEMARK OFFICE
CERTIFICATE OF CORRECTION

PATENT NO. : 5,314,432
DATED : May 24, 1994
INVENTOR(S) : Kamaljit S. Paul

It is certified that error appears in the above-indentified patent and that said Letters Patent is hereby corrected as shown below:

Col. 4, line 26, after "axial" insert
--tomographic cuts are obtained by C.T. scan through--

Signed and Sealed this

Sixth Day of September, 1994

Attest:

BRUCE LEHMAN

Attesting Officer

Commissioner of Patents and Trademarks